(12) United States Patent
Weston

(10) Patent No.: US 6,222,090 B1
(45) Date of Patent: *Apr. 24, 2001

(54) WATERPROOF INJECTION PORT COVER

(75) Inventor: Sharon Weston, Boca Raton, FL (US)

(73) Assignee: Shower-Seal, Inc., Boca Raton, FL (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/072,265

(22) Filed: May 4, 1998

Related U.S. Application Data

(60) Provisional application No. 60/045,594, filed on May 5, 1997.

(51) Int. Cl.$^7$ ......................................................... A61F 13/00
(52) U.S. Cl. ................................. 602/41; 602/52; 602/54; 602/55
(58) Field of Search ......................... 602/41–59; 128/888, 128/889; 604/174, 175, 179, 180; D24/189

(56) References Cited

U.S. PATENT DOCUMENTS

| Re. 31,887 | * | 5/1985 | Hodgson | 428/355 |
| 5,152,282 | | 10/1992 | Elphick et al. | . |
| 5,415,642 | * | 5/1995 | Shepard | 604/180 X |
| 5,495,856 | * | 3/1996 | Fentress | 128/846 |
| 5,780,048 | * | 7/1998 | Lee | 424/443 |

\* cited by examiner

Primary Examiner—Kim M. Lewis
(74) Attorney, Agent, or Firm—Ted W. Whitlock

(57) ABSTRACT

A protective cover for keeping dry an area of an animal body during bathing, showering, or swimming is disclosed. One embodiment of the protective cover includes a flexible waterproof sheet having a waterproof adhesive provided around the edge of the sheet to affix the sheet to the body and prevent water or moisture from contacting the area to be kept dry. Another embodiment includes a cover having a raised area so the cover does not contact the area of the body to be kept dry. Methods of use are also described.

7 Claims, 3 Drawing Sheets

WATERPROOF INJECTION PORT COVER

CROSS-REFERENCE TO RELATED APPLICATIONS

This application is a continuation-in-part of Applicant's provisional patent application, Ser. No. 60/045,594, which was filed on May 5, 1997 now abandoned.

BACKGROUND OF THE INVENTION

Treatment of certain diseases or conditions in patients can require frequent administration of medication or other fluid directly into the bloodstream of that patient. Frequent intravenous administration had previously been observed to cause or exacerbate complications. For example, repeated injection over a protracted period of time can cause damage to a blood vessel, e.g., collapse of a vein, which can render further or subsequent injection more difficult or painful.

Attempts to remedy such undesirable effects of frequent injection have come in the form of placement of a catheter into a blood vessel, e.g., a vein, wherein the catheter has a cannula portion which is placed inside the vessel and an injection port which remains outside the body and is accessible for frequent injection by a hypodermic needle and syringe or continuous drip or infusion pump. Although catheterization of the vessel can ameliorate damage to the vein, it does not completely eliminate the potential collapse or other damage to the vessel. Moreover, exposure of the injection port to the environment outside the skin can increase the susceptibility of contamination or infection at the wound site, or sepsis of the patient due to bacteria or other micro-organisms entering the site or blood stream via the catheter.

Recently, catheters have been developed which have a cannula portion which inserts into the blood vessel and an injection port for delivery of medication and fluids wherein the entire cannula and injection port are placed completely under the skin. These are well known in the art as "implantable access systems" and are commercially available, for example, as PORT-A-CATH and P.A.S. PORT systems (SIMS Deltex, Inc., St. Paul, Minn.). These systems are described in one or more of the U.S. Pat. Nos. 4,887,414 and 4,963,133 which are hereby incorporated by reference.

The PORT-A-CATH system is placed under the skin with the catheter inserted into a vein in the chest. The tip of the catheter is inserted into a vein and the delivery tip positioned at a point just above the heart. The injection port can be placed at a convenient place under the skin, e.g., above the pectoral muscle. The P.A.S. PORT system is typically placed under the skin with the catheter placed into a vein in the lower arm. The tip of the catheter is located in a vein at a point just above the heart, similar to that PORT-A-CATH system. The access port of the P.A.S. PORT system is positioned under the skin and above a muscle in the forearm.

To access either system, a specially designed non-coring needle can be inserted through the skin directly into an access port comprising a septum. The access port in an implantable access system comprises a small metal chamber which is sealed at the top by a septum made of self-sealing silicone. The housing of the port can be made from medical-quality metal, e.g. titanium, or other medically acceptable rigid material. The cannula or catheter portion can be a thin flexible tube made from silicone or polyurethane. These materials are known for their long, useful life when placed inside the human body.

Although these implantable access systems can reduce the risk of infection, the systems are not without certain disadvantages. For example, care of the system can require frequent flushing with an anticoagulant, e.g., heparin solution to prevent blood clotting, especially after injection or infusion when blood may enter the system during administration of a medication. In addition, during an infusion, a needle or catheter is continuously in place during treatment and requires that a dressing be used to cover the needle or catheter injection site. The dressing secures the catheter in position and helps to keep the injection site clean.

One example of a stabilization dressing is Veni-Gard® (Con-Med Patient Care Systems, Utica, N.Y.). The Veni-Gard stabilization dressing comprises a sterile, transparent polymeric sheet having an adhesive disposed on one face which contacts the skin and catheter in order to stabilize the catheter, and a cushioned adhesive strip affixed around its periphery to secure the dressing in place. These, and other dressings indicated for use on surgical sites, e.g., Tegaderm (3M Corneal epithelial erosion., Minneapolis, Minn., USA) and OpSite Flexgrid (Smith & Nephew, Hull, England), can be disadvantageous in that the adhesive can stick to the catheter insertion site, to the incision, or to any tape, stitches, or staples used to close the incision. The medical professional applying the dressing must therefore "wet" the site prior to application of the dressing to prevent adherence at any undesired site or to any component of the catheter system.

Moreover, these stabilization or surgical dressings are not completely waterproof, and typically would not allow the user to bathe or shower without getting the site wet, risking contamination or infection of the site. These dressings are not indicated as a waterproof seal for use during bathing or showering, and have not been suggested for such use or for implantable access systems. Keeping the dressing dry can thus hamper the patient's ability to bathe or shower in a normal fashion.

Although medical professionals have, in the past, recommended covering the dressing with a plastic bag or other waterproof or water resistant sheet material taped over the dressing during bathing, there has heretofore been no such article available that can successfully keep water from the area intended to be kept dry. Patients have found that taping a plastic bag or other waterproof or water-resistant sheet material over the dressing is only minimally successful. Water from the bath or shower can often leak or seep into the area to predispose the injection site to contamination or infection.

Thus, there is a need for providing a means for keeping an area on the body dry during bathing or showering, wherein the body area is a surgical site, catheterization site, or injection port site. Such an article or method for use with an implantable access system would be highly desired and advantageous.

BRIEF SUMMARY OF THE INVENTION

It is an object of the subject invention to provide a cover for keeping dry an injection site or a dressing covering an injection site during an infusion treatment using an implantable access system.

It is another object of the subject invention to provide a waterproof cover for a surgical incision area on the body which is intended to be kept dry during bathing or showering. The area can be covered during a bath or shower with a waterproof or water-resistant cover according to the subject invention, thereby achieving the desired result.

It is a further object of the subject invention to provide a waterproof cover for protecting an area of the body against harm or inconvenience, e.g., contamination or infection, caused by exposure of the area to water during bathing or showering.

In one embodiment of the invention, an article of manufacture is provided which comprises a light-weight sheet forming a cover, the sheet having adhesive disposed in a particular pattern on one face of the cover. The face having adhesive disposed thereon is the face which contacts the skin of the wearer, and is termed the "front face." Preferably, the adhesive is disposed around the perimeter of the front face of the sheet, leaving a central, adhesive-free area on the front face of the sheet so that adhesive does not come into contact with the surgical, injection port, or catheter site being covered. The back face of the sheet is adhesive-free.

In another embodiment, the protective cover according to the subject invention can comprise a material substantially rigid enough to retain its shape so that the cover is raised or "bubbled" in relation to the surface plane of the body and therefore does not touch or otherwise come in contact with the area that is being protected against water or moisture. At the same time, the raised configuration cover is preferably at least partially flexible, which advantageously allows the cover to conform to the shape of the body when placed in its position of use.

A further embodiment of the subject protective cover comprises a flange about the perimeter of the cover so that an adhesive can be disposed thereon or adhesive tape can be affixed thereto in order to facilitate affixing the article to the skin and thereby keep the cover in place.

The cover can be taped into place, preferably using a waterproof adhesive tape. Alternatively, the protective cover can have an adhesive disposed in a particular pattern on the front face of the sheet or flange. The protective cover can further be provided with a removable adhesive covering, e.g., a strip of paper, plastic, or other similar material, to cover the adhesive until time of use. For example, a peel-off cover for the adhesive area can be employed similar to peel-off coverings used in conjunction with the adhesive portion of a bandage strip, e.g., BAND-AID strips.

Methods of use for the subject protective cover are also described herein. For example, the protective cover according to the subject invention can be used in a method for protecting an area of the body from becoming wet or moist when bathing, showering, or swimming. A further advantage of the subject invention comprises protecting against water or moisture on an area of the body that has a medical dressing protecting an injection or infusion port. The injection site or infusion port protected by the subject article or method can be part of an implantable access system. The method of the subject invention can also be applied to protect a wound or surgical incision area that is required to be kept dry for certain periods of time.

DETAILED DESCRIPTION OF THE INVENTION

Figure 1:
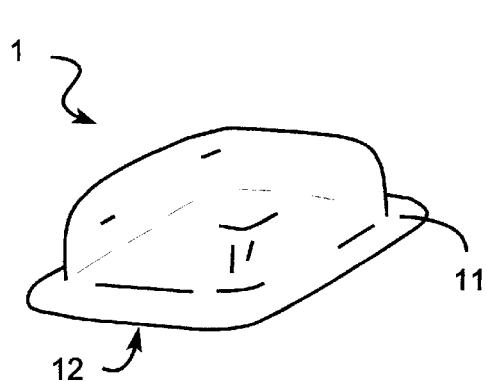
FIG. 1 shows a perspective view of a substantially rectangular protection cover according to the subject invention.

The subject invention concerns a cover or shield for an area of the body in need of protection against water or moisture. For example, the subject invention can be used to keep the desired area dry when showering, bathing, or swimming.

In a preferred embodiment, the subject device comprises a sheet of material which is compatible with contacting the skin for an extended period of time, e.g., days or weeks. The material can be plastic or other polymeric material so long as it is waterproof. The terms "waterproof", "water-tight", and "water-resistant" are herein used interchangeably. Preferably, the material is vinyl, and most preferably is 100% virgin vinyl, which is commercially available. Such material is also compatible with heat or gas sterilization procedures.

The sheet can be any practical shape or size so that it completely covers the area needed to be kept dry. Typically, the subject article is rectangular, ranging in size from about two inches square up to about ten inches or more, if necessary, in any one linear dimension. Being a substantially flat sheet, the subject article is substantially without dimension in thickness, but is preferably of a thickness or "weight" which is durable enough to prevent it from easily being punctured or torn, but flexible enough to conform to the area of the body on which it is placed. Preferably, the thickness is about 0.09 mil or less. It would also be well understood by those of ordinary skill in the art that the subject article can be provided in other non-rectangular shapes, including circular, oval, or elongate in accordance with the area to be covered.

In the preferred embodiment, an adhesive can be disposed on one face of the sheet for affixing the article to the skin and forming a watertight seal. The adhesive is preferably a waterproof adhesive, e.g., Transpore (3M Company, Minneapolis, Minn. USA) or an equivalent. Advantageously, the adhesive for the preferred embodiment of the subject article is disposed in a particular pattern such that the entire periphery of the sheet has adhesive disposed thereon, but a central area of the sheet is adhesive-free so that the sheet does not adhere to the site being covered, only adhering around the site.

Preferably, the adhesive is disposed in a pattern wherein the adhesive forms a continuous border around the periphery of the sheet for forming a waterproof seal around the edges of the sheet when placed in position over the site. The adhesive border is preferably about one-half inch or less in width, and more preferably between about three-eighths and about one-quarter inches in width. A most preferred width for the adhesive border is about three-eighths inches.

Alternatively, an adhesive border can be provided as a separate component from the sheet, e.g., an adhesive strip or tape which can be overlain on each edge of the sheet to form a continuous border and waterproof seal.

In a most preferred embodiment, the adhesive border is faced with a releasable sheet or strip for covering the adhesive, preventing inadvertent adherence to areas which the article is not intended to be affixed, and to maintain its adhesive properties for maximum function when used.

In another embodiment, the subject invention can comprise a cover or shield having an outer, substantially convex side and an inner, substantially concave side forming a bubble-like article, having a peripheral edge which contacts the skin to form a substantially waterproof or water-resistant seal against water or moisture from the outside environment. The protective shield can be held in place by an adhesive, for example, adhesive tape, which preferably is itself waterproof or water-tight or water-resistant.

The waterproof adhesive tape can be affixed to the protective shield and to the skin to form a water-tight seal around the entire periphery of the protective cover. Alternatively, the protective shield can be taped or strapped transversely across the convex side of the shield to hold the shield in place in a manner to form the water-proof seal. In addition, a separate adhesive or sealing composition can be disposed on one face of the protective cover, preferably along a peripheral edge of the face contacting the skin of the wearer, for forming a water-tight seal.

In a further embodiment, the subject invention can comprise a protective shield which further comprises a flange formed integrally with the shield around the periphery of the protective cover. The flange can be used as a tab to facilitate attachment of an adhesive tape thereto, or can comprise on a peripheral edge of its skin-contacting face a waterproof adhesive which can seal against the skin when pressed into place. This embodiment of the subject invention resembles the transparent plastic covering in bubble-pack packaging, which is a well-recognized means for packaging articles for sale.

The protective cover of the subject invention can be manufactured in various shapes and sizes in accordance with a desired area of coverage or protection. For example, the bubble portion of the subject article can be raised an appropriate distance from the body surface plane to accomplish certain desired results. Specifically, the bubble portion can be raised at an appropriate distance, e.g., approximately 1/16 to about two inches, to avoid contact with the skin or a raised area of the skin. A raised area of the skin can result from use of an implantable access system wherein the injection or infusion port is surgically placed under the skin leaving a raised area surrounding the implanted injection or infusion port. In addition, a raised area of the skin can be due to an abrasion, a healing wound, or a surgical incision which preferably remain untouched by the protective cover.

Preferably, in the bubble embodiment of the subject protective cover, the raised area is formed at a height that does not preclude it from being comfortably and inconspicuously worn under clothing. A most preferred height for the protective cover of the subject invention is approximately one inch.

The bubbled embodiment of the protective cover according to the subject invention can also be made in various shapes to cover a particular area of the body which is to be protected. For example, a substantially circular or oval shape can be used for covering a small or substantially circular wound, opening, or an injection port for an implantable access system. The protective cover can also be substantially elongate or substantially rectangular having rounded edges or corners to cover and protect a linear incision or wound. The shape of the protective cover can also be customized to cover a particular irregularly shaped area of the body intended to be protected wherein the area is not adequately protected by a substantially circular, rectangular, elongate, or ovate cover.

The invention can perhaps best be understood by reference to the accompanying figures. FIG. 1 shows a substantially rectangular, or square, protective cover according to the subject invention having a raised "bubble" housing 10 and an integrally formed flange 11 for facilitating attachment of the protective cover to the body. The flange can be formed from the same material as the protective cover and can be provided without adhesive. In such an embodiment, the protective cover can be taped or strapped in place using waterproof or water-protective adhesive tape or other attachment means that serves the same or a similar purpose as adhesive tape.

Figure 5:
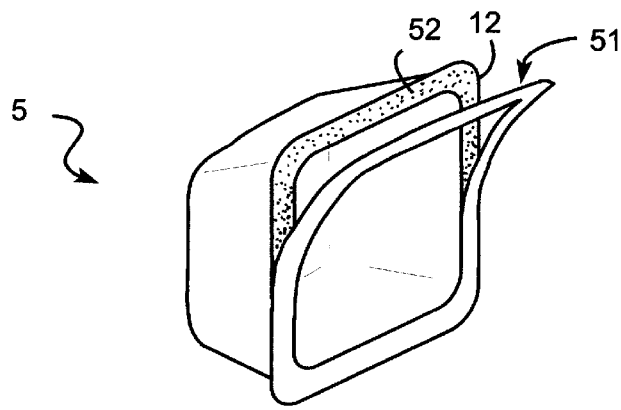
FIG. 5 shows an embodiment of a protective cover of the subject invention having a peel-off covering for protecting an adhesive applied to the flange of the protective cover.

Alternatively, the flange 11 can be provided with an adhesive applied directly thereto such that the protective cover 1 can be directly applied to the body and positioned over the area in need of protection. In a preferred embodiment, the adhesive can be applied to the flange on the face 12 of the flange, which contacts the body. In a preferred embodiment, 5 as shown in FIG. 5, a peel-off covering 51 for the adhesive, having a shape substantially identical to the flange, can be provided over the flange adhesive 52 in order to retain the adhesive properties of the adhesive material until ready for use. It would be well-understood in the art that other protective covers for the adhesive can be used in accordance with the subject invention.

Figure 2:
FIG. 2 shows a perspective view of a substantially circular embodiment of a protective cover according to the subject invention.
Figure 3:
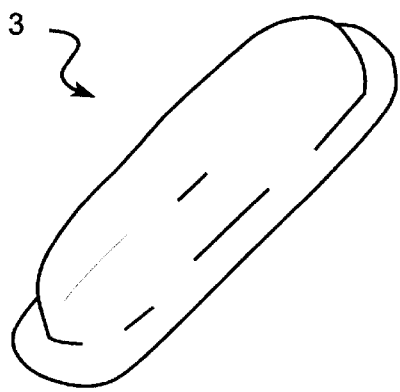
FIG. 3 shows a perspective view of a substantially elongated protective cover according to the subject invention.
Figure 4:
FIG. 4 shows a perspective view of a substantially circular protective cover according to the subject invention.

FIG. 2 shows a substantially circular protective cover 2. It would be readily understood that the outer face of the protective cover in any of the described embodiments can be substantially flat or, alternatively, can be domed. FIG. 3 shows a substantially elongated protective cover 3 that can be used for protection of a longitudinal incision. FIG. 4 shows a substantially ovate protective cover 4 which can be useful for protecting an area of the body, for example, a surgical area following a mastectomy.

Each of the above embodiments is shown having a flange for facilitating attachment of the protective cover to the body. Persons of ordinary skill in the art would recognize that other tabs or flange-like means can be used to achieve a facilitated attachment. In addition, it would be well understood that each of the embodiments can be provided without a flange.

The protective cover of the subject invention can be made using an appropriate material for contacting skin. For example, an inert plastic or polymer material frequently used on a patient or the skin of a patient can be employed. Preferably, the material can be rigid enough to maintain its shape, but can be flexible enough such that it can be formed or conformed to a particular shape of the body surface plane when placed in position. The material used for the subject protective cover can be opaque, translucent, or, preferably, transparent so that a wearer of the protective cover can monitor the area for seepage of water or moisture into the protected area. Clearly, in order to accomplish its intended function, the protective cover of the subject invention is substantially solid, i.e., without air holes or pores which could allow water to enter the protected area. The protective cover can also be provided with a decorative design or color for aesthetic or other purposes. A person of ordinary skill in the art would recognize that various materials having particular properties for medical use could be used in accordance with the subject invention.

In a preferred embodiment, wherein the subject protective cover comprises a plastic or polymer material, the invention can be molded to achieve a desired shape and size. Molding procedures are readily available and known to those of ordinary skill in this art.

Figure 6A:
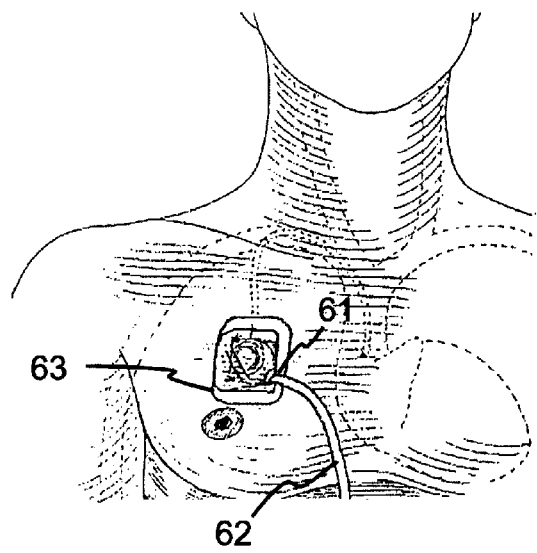
FIG. 6A shows a protective cover according to the subject invention placed over an injection port (in phantom) placed under the skin of the chest of a patient.
Figure 6B:
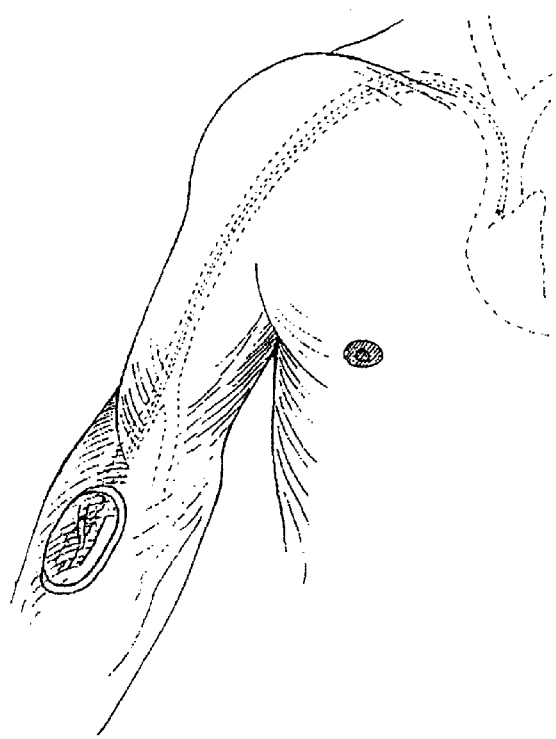
FIG. 6B shows a protective cover according to the subject invention placed over an injection port (in phantom) placed under the skin of the forearm of a patient.

Use of the protective cover can also be readily understood in view of the description and drawings provided herein of the manufactured article in accordance with the subject invention. Specifically, the protective cover of appropriate size and shape can be provided to the patient, placed over the area in need of protection, and secured in place by a waterproof adhesive. Examples of placements for the protective cover are illustrated in FIGS. 6A and 6B. FIG. 6A further illustrates the embodiment comprising a port or slot 61 described hereinbelow, which can accommodate a tube 62 passing through the wall of the protective cover housing.

A sealing means 63, e.g., a grommet, can be included to engage the housing and tube in a water-tight manner. The patient can then bathe or shower or swim in a normal manner without the risk of exposing the protected area to water or moisture. In the flangeless embodiment of the protective cover, an adhesive composition can be placed on the skin or the peripheral edge of the cover, conforming to the shape of the cover, and the cover can then be placed in position to secure it over the protected area.

In a preferred embodiment having a flange integrally formed with the cover, a waterproof or water-protective tape can be applied around the peripheral edge of the flange to secure the cover in place over the protected area in a waterproof or water-tight manner. In a most preferred embodiment, the integrally formed flange can have an adhesive substance substantially covering the face which is placed against the skin so that the protective cover can be positioned over the protected area, and pressed into place to form a water-tight or waterproof seal around the peripheral edge of the cover. Adhesive tape or a strap or other attachment means can be used in addition to the flange adhesive to ensure a water-tight or waterproof seal and maintenance of the placement of the protective cover.

A further embodiment of the subject invention comprises a port or slot formed in the protective cover to allow for a drainage tube or injection tube to traverse the peripheral edge of the protective cover so that a portion thereof can remain outside the protective cover. For example, in a wound having substantial edema, a drainage tube can be placed in the wound wherein the drainage tube can exit the protective cover. In addition, in certain treatments using an infusion pump, a tubing or catheter is typically connected from the pump to a needle insertable into the septum of the implantable access system. The port or slot can allow passage of the infusion pump tubing through the housing of the protective cover of the subject invention in a water-tight manner. Preferably, a grommet, washer, or other sealing means can be positioned in the port or slot to form a waterproof seal within the port or slot.

In a preferred embodiment, the grommet or sealing means can be substantially tubular to allow the drainage tube to pass therethrough in a water-tight manner. For example, the aperture in the tubular grommet can be of a size such that it frictionally engages the exiting tube in a manner to form a water-tight seal.

Figure 7A:
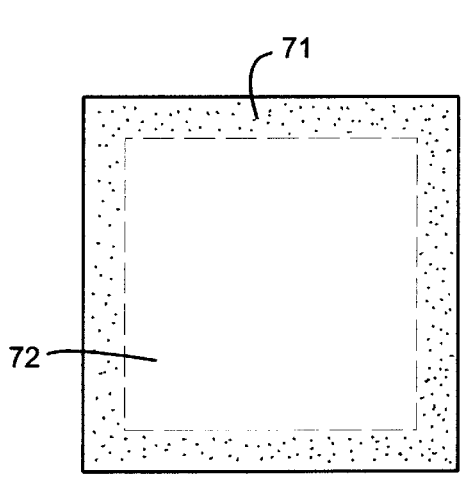
FIG. 7A shows a plan view of a front face of an embodiment of the subject article wherein the article comprises a substantially flat flexible sheet having adhesive disposed on its peripheral edge, and a central adhesive-free area.
Figure 7B:
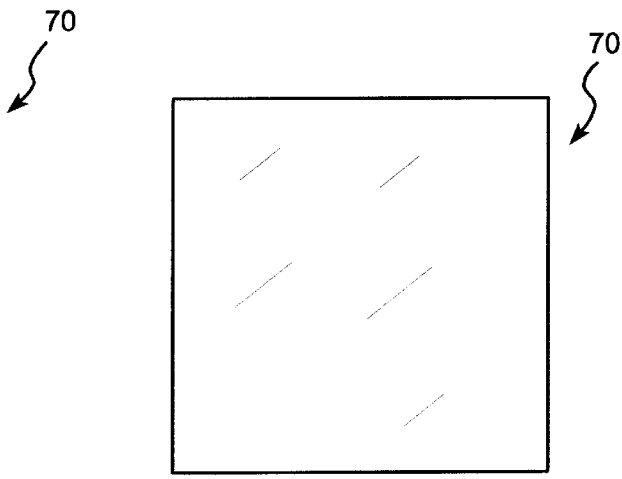
FIG. 7B shows a plan view of a back face of the article shown in FIG. 7A.
Figure 7C:
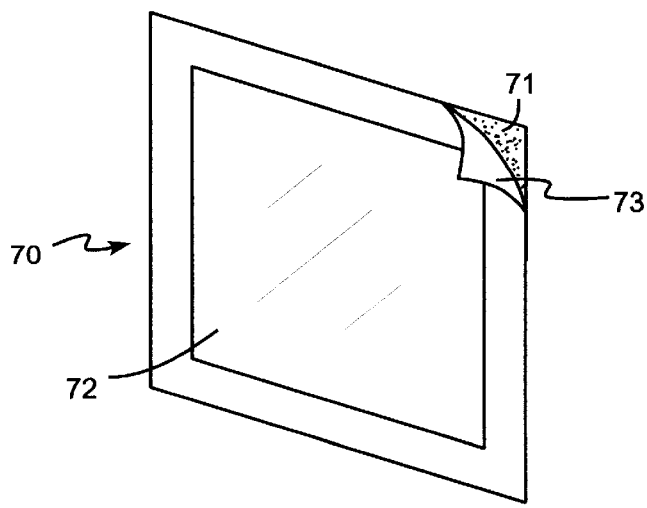
FIG. 7C shows a perspective view of the embodiment shown in FIG. 7A, illustrating a removable cover for protecting the adhesive prior to use.

As shown in FIGS. 7A–7C, one embodiment of the subject invention comprises a sheet 70 of a waterproof material, e.g., vinyl or polymeric material, having an adhesive 71 disposed on a peripheral border of the sheet 70 (FIG. 7A). Advantageously, an adhesive-free area 72 is provided on the sheet 70 which can come into contact with the site being covered without adhering thereto.

FIG. 7B shows a back, or outer, face of the sheet 70 which is substantially adhesive-free.

FIG. 7C illustrates the sheet embodiment of the subject article having a releasable adhesive-facing sheet or strip 73 for protecting and maintaining the integrity of the adhesive until the article is ready to be applied to the skin. The releaseable sheet or strip 73 can be provided in a configuration which conforms to the pattern of the adhesive or can cover the entire front face of the sheet, i.e., covering the adhesive 71 and the central adhesive-free area 72.

The releaseable facing sheet or strip is formed by applying an adhesive-release material, e.g., silicone, on a facing sheet prior to matching the facing sheet to the subject article. The adhesive-release material advantageously bonds to the adhesive enough such that the removable sheet or strip is retained in position, but is easily removed from the adhesive without affecting the adhesive properties of the adhesive.

The waterproof sheet having adhesive disposed thereon can be manufactured in a variety of ways. Preferably, a sheet of material, e.g., vinyl, is provided whereby the sheet is large enough to be cut into a plurality of sheets which form the subject article. Alternatively, the sheet can be a laminate having waterproof material as the outer layer or layers. Liquid adhesive is disposed onto one face of the sheet by spraying or other conventional applicating procedure. According to one method of manufacture, adhesive can be applied to the single large sheet comprising a plurality of subject articles in a pattern such that each article, when cut to size, has an adhesive border. Alternatively, the single large sheet can be cut to form the subject articles, followed by application of adhesive in the desired pattern.

The subject articles can be conveniently packaged for sale, e.g., in individual packages for single use. Preferably, the articles are packaged such that they can be gas or heat sterilized according to conventional procedures. The user can then open the sterile package, remove the removable adhesive-protecting sheet or strip, and apply the article to the site to form a watertight seal around the site. The user can then bathe or shower without exposing the site to water or moisture.

The invention can take other specific forms without departing from the spirit or essential attributes thereof for an indication of the scope of the invention. The following Example is for illustrative purposes only and should not be construed or in any way limiting of the invention as described herein.

EXAMPLE

Indications for Use

Below are tabulated typical size configurations and suggested uses for the article according to the subject invention:

| Application Size | Estimated Patient Need | Suggested Use | Features | Patient Benefits |
| --- | --- | --- | --- | --- |
| 4 × 4 | 4 days | Pacemaker Patient | Waterproof surgical site | Enables patient to shower with ease while wearing a bandage over the surgery site |
| 5 × 7½ | 10 days to 2 weeks | Shoulder replacement Rotator cuff surgery Stomach incision Back surgery Gyn laparoscopy Breast Hernias Gallbladder | Waterproof bandaged site | Allow patient to shower with comfort and confidence during time of recovery |

-continued

| Application Size | Estimated Patient Need | Suggested Use | Features | Patient Benefits |
| --- | --- | --- | --- | --- |
| 4 × 9 | 3 days to 10 days | Vascular Orthopedic: knee, leg, arm, and shoulder | Flexible waterproof application | Simple protection for showering with ease |
| 6 × 7½ | 6 weeks to 7 months | Chemotherapy patient or aids patient wearing a port-a-cath | Waterproof the port-a-cath while activated | Allows patient to shower with confidence and comfort during treatment or while port-a-cath is activated |
| 4 × 9 | 3 weeks to 5 weeks | Surgical site coverage | adhesive-free area in center of sheet | area is not required to be moistened to prevent adherence of adhesive |

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A protective cover for keeping an area of a body of a person free of water and moisture, said cover consisting essentially of
   a substantially flat, single layer of a flexible sheet of waterproof and moisture-proof material which completely covers a site intended to be unexposed to water or moisture, said flexible sheet having a front face wherein the entire surface of the front fare contacts the body of the person when said cover is in use; and
   a single annular layer of waterproof and moisture-proof adhesive disposed continuously around a peripheral edge of said front face of said sheet, leaving a central adhesive-free area on the front face of said sheet.

2. The protective cover of claim 1, wherein said cover has a continuous border of adhesive about three-eighths inches plus or minus one-eighth inches in width.

3. The protective cover of claim 2 wherein said continuous border of adhesive is about three-eighths inches wide.

4. The protective cover of claim 1 wherein said sheet is about 0.09 mil or less in thickness.

5. The protective cover of claim 1 wherein said cover further comprises a removable sheet or strip comprising an adhesive-release material for protecting adhesive until time of use.

6. The protective cover of claim 5 wherein said removable strip or sheet substantially conforms to the pattern of adhesive disposed on the front face of said sheet.

7. The protective cover of claim 1 wherein said cover is sterilizable.

* * * * *